United States Patent
Greenberg et al.

(10) Patent No.: US 10,431,331 B1
(45) Date of Patent: Oct. 1, 2019

(54) COMPUTER-EXECUTABLE APPLICATION THAT IS CONFIGURED TO PROCESS CROSS-CLINICAL GENOMICS DATA

(71) Applicant: Allscripts Software, LLC, Raleigh, NC (US)

(72) Inventors: Eyal Greenberg, Meitar (IL); Shiri Ben Tal, Omer (IL); Assaf Halevy, Pittsburgh, PA (US); Joel Diamond, Pittsburgh, PA (US); Robert Wartenfeld, Tel Aviv (IL); Davis Walp, Weston, MA (US); Jeri-lynn Gehr, Raleigh, NC (US); Gary Gartner, Durham, NC (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 532 days.

(21) Appl. No.: 15/231,971

(22) Filed: Aug. 9, 2016

Related U.S. Application Data

(60) Provisional application No. 62/300,896, filed on Feb. 28, 2016.

(51) Int. Cl.
*G16H 10/60* (2018.01)
*G16H 40/63* (2018.01)

(52) U.S. Cl.
CPC ............. *G16H 10/60* (2018.01); *G16H 40/63* (2018.01)

(58) Field of Classification Search
CPC ........ G06Q 50/22; G06Q 50/24; G06F 19/00; G06F 19/10; G06F 19/18; G06F 19/24; G06F 19/26; G06F 19/30; G06F 19/32; G06F 19/36; G16H 10/00; G16H 10/40; G16H 10/60; G16H 15/00; G16H 50/00; G16H 50/20; G16H 50/70
USPC ........................................................ 705/2, 3
See application file for complete search history.

(56) References Cited

U.S. PATENT DOCUMENTS

| | | | |
|---|---|---|---|
| 7,613,621 B2 * | 11/2009 | Brown .................. | G06F 19/325 705/2 |
| 2002/0004729 A1 * | 1/2002 | Zak ........................ | G16H 10/60 705/3 |
| 2003/0046114 A1 * | 3/2003 | Davies .................. | G06Q 10/10 705/3 |
| 2004/0243435 A1 * | 12/2004 | Williams ........... | G06Q 10/0637 705/2 |
| 2005/0075543 A1 * | 4/2005 | Calabrese .............. | G06Q 30/02 600/300 |
| 2005/0131741 A1 * | 6/2005 | Tang ..................... | G06F 19/325 705/2 |
| 2008/0131887 A1 * | 6/2008 | Stephan ................. | G16B 20/00 435/6.11 |
| 2008/0195326 A1 * | 8/2008 | Munzer .................. | G06F 19/28 702/20 |
| 2010/0063837 A1 * | 3/2010 | Bellante .............. | G06Q 10/105 705/2 |

(Continued)

*Primary Examiner* — Jason S Tiedeman
(74) *Attorney, Agent, or Firm* — Medley, Behrens & Lewis, LLC

(57) ABSTRACT

Described herein are various technologies pertaining an electronic health record application (EHR). The EHR has a rules engine that is configured to execute a plurality of rules corresponding to respective genetic disorders. The rules receive clinical data as input, and each rule is configured to output an indication as to whether or not a patient is a candidate for genetic testing for a genetic disorder.

20 Claims, 12 Drawing Sheets

(56) References Cited

U.S. PATENT DOCUMENTS

| | | | |
|---|---|---|---|
| 2011/0105852 A1* | 5/2011 | Morris | G06Q 10/10 600/300 |
| 2012/0259657 A1* | 10/2012 | Keynan | G06F 19/00 705/2 |
| 2013/0197060 A1* | 8/2013 | Markel | A61K 31/7105 514/44 A |
| 2013/0253348 A1* | 9/2013 | Tremper | A61B 5/02055 600/508 |
| 2013/0282404 A1* | 10/2013 | Janevski | G06F 19/325 705/3 |
| 2014/0108040 A1* | 4/2014 | Belcher | G06Q 50/22 705/2 |
| 2014/0222400 A1* | 8/2014 | Coleman | G06F 19/3462 703/2 |
| 2014/0288969 A1* | 9/2014 | Goltra | G16B 20/00 705/3 |
| 2014/0316821 A1* | 10/2014 | Sheffield | G06Q 50/22 705/3 |
| 2015/0269337 A1* | 9/2015 | Schulte | G06Q 50/24 705/3 |
| 2015/0307947 A1* | 10/2015 | Basu | C12Q 1/6886 506/2 |
| 2015/0331995 A1* | 11/2015 | Zhao | G06F 19/321 705/2 |
| 2018/0122517 A1* | 5/2018 | Bessette | G16H 20/30 |

* cited by examiner

| LDLR | |
|---|---|
| LOW DENSITY LIPOPROTEIN RECEPTOR | HGNC: 6547 |
| LDLR RECEPTOR | ENTREZ GENE: 3949 |
| LDLR CLASS A DOMAIN-CONTAINING PROTEIN 3 | ENSEMBL:ENSG... |
| | OMIM: 606945 |
| FHC | UNIPROTKB: P01130 |
| FH | |

210

| P | g.36045C>A, c.2043C>A, 1606+192C>A dbSNP: rs121908031 |
|---|---|
| LP | g.21186_21187insTG |
| VUS | g.28905C>T... |
| LB | g.35741C>T... |
| B | g.5228C>T... |
| RF | g.30221G>A |
| ... | |

302

| Sequencing Candidates | | | | | |
|---|---|---|---|---|---|
| Familial Hypercholesterolemia ⌄ | Filter by: Sex⌄ Age⌄ Score⌄ Reason⌄ LDL⌄ PCR⌄ | | | | |
| Patient | Score⌄ | Reason | LDL (Latest) | PCP | Last Updated |
| Cornell, Kezra 56y\|24-Apr-1960 F | 89 | LDL 320 mg/dl, Premature CHD | 320 mg/dl | Dr. James Medicine | 16-Jan-2016 |
| Erwin, Jack 42y\|12-May-1973 M | 89 | LDL 340 mg/dl, Premature CHD | 340 mg/dl | Dr. James Medicine | 06-Jan-2016 |
| Gardner, Sean 56y\|28-Jun-1960 M | 89 | LDL 370 mg/dl, Premature CHD Reason 3, Reason 4, Reason 5 | 310 mg/dl | Dr. Rebecca Lane | 06-Jan-2016 |
| Lin, Leye 76y\|02-Sep-1940 M | 89 | LDL 280 mg/dl, Vascular Disease | 280 mg/dl | Dr. James Medicine | 26-Jan-2016 |
| Smith, John 71y\|18-Jan-1944 M | 89 | LDL 350 mg/dl, Premature CHD | 350 mg/dl | Dr. James Medicine | 26-Jan-2016 |
| Andrews, Ashley 60y\|31-Oct-1956 F | 87 | LDL 340 mg/dl, Premature CHD | 340 mg/dl | Dr. Rebecca Lane | 26-Jan-2016 |

FIG. 9 even if an EHR
COMPUTER-EXECUTABLE APPLICATION THAT IS CONFIGURED TO PROCESS CROSS-CLINICAL GENOMICS DATA

RELATED APPLICATION

This application claims priority to U.S. Provisional Patent Application No. 62/300,896, filed on Feb. 28, 2016, and entitled "COMPUTING SYSTEM THAT PRESENTS DATA BASED UPON PANOMICS", the entirety of which is incorporated herein by reference.

BACKGROUND

Electronic health record applications (EHRs) are robust applications that are utilized in medical facilities across a variety aspects of a medical practice. For example, and not by way of limitation, an EHR can include functionality related to patient intake, billing, updating medical records, prescribing medication, tracking care over time, and so forth. Conventional EHRs, however, are not configured to handle molecular or genomics data. Further, even if an EHR is configured to present genetic test results for a patient to a primary care provider, typically, primary care providers have difficulty interpreting such results.

SUMMARY

The following is a brief summary of subject matter that is described in greater detail herein. This summary is not intended to be limiting as to the scope of the claims.

Described herein are various technologies related to a computer-executable application that is configured to process cross-clinical genomics data. In an example, the application can be an electronic health record application (EHR). In another example, the application can be configured to interact with an EHR (e.g., as a supplement to functionality provided by the EHR). Functions that are performable by the application include, but are not limited to including, 1) identifying that a patient may benefit from genetic testing at the point of care; 2) identify a list of patients that may benefit from genetic testing; 3) receive genetic results in a structured format and present interpretations of the genetic results to a clinician. These functions are enabled based upon an ontology that relates clinical terms to genomic terms, a knowledge base that includes information pertaining to genetic terms, and genetics data that can be received from a genetics computing device, where the genetics data has a structured format.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE DRAWINGS

FIGS. 2-3 illustrate portions of an ontology.

FIGS. 4-10 depict graphical user interfaces that can present information relating to genetics.

DETAILED DESCRIPTION

Figure 1:
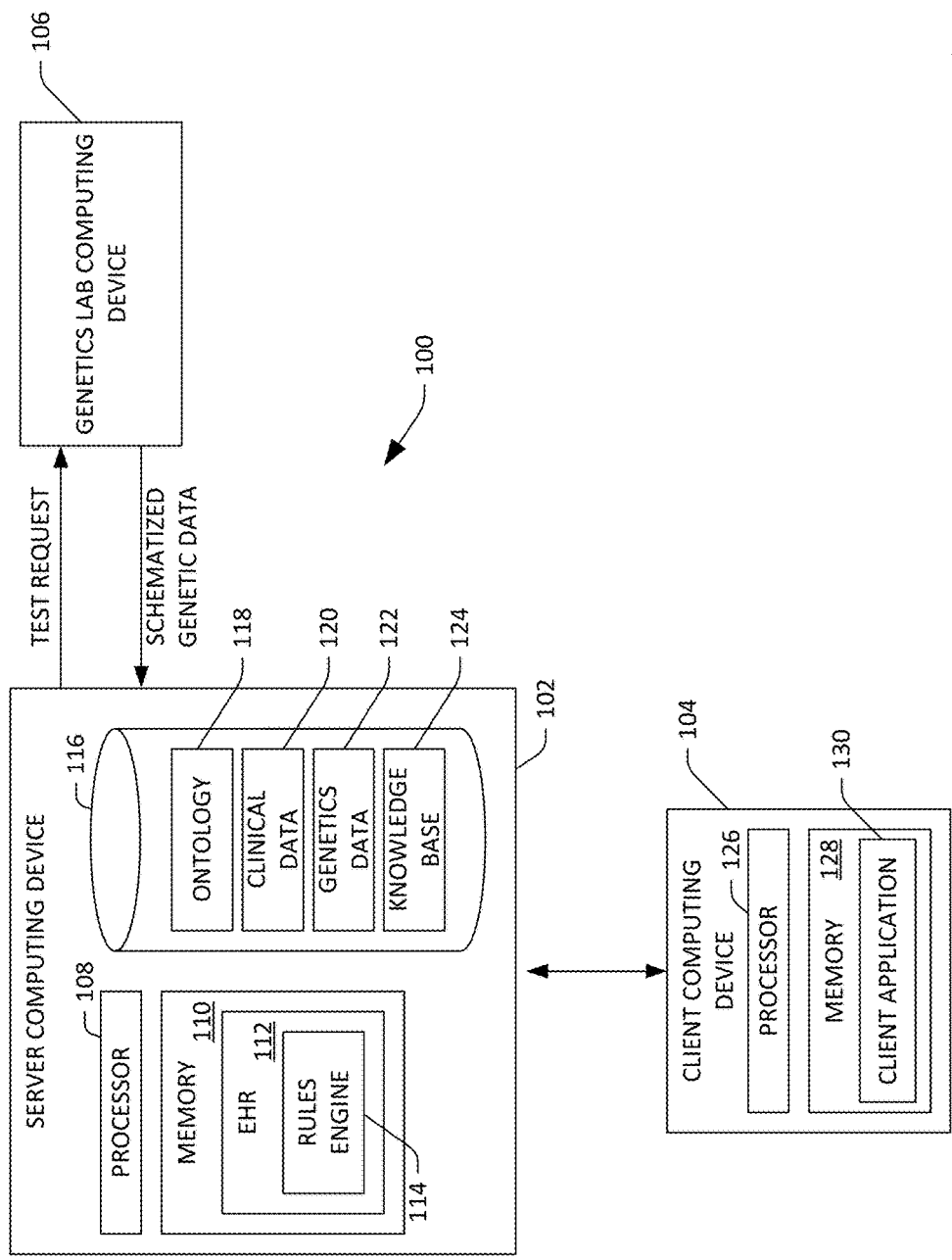
FIG. 1 is a functional block diagram of an exemplary computing system, wherein a computer-executable application is configured to process genetics data.

Various technologies pertaining to a computer-executable application that is configured to process cross-clinical genomics data are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

Now referring to FIG. 1, an exemplary system 100 that facilitates executing a computer-executable application, wherein such application is illustrated, wherein the application is configured to provide information pertaining to panomics to a clinician at the point of care for the patient. The term panomics is intended to encompass omics, including genomics, proteomics, metabolomics, etc. As shown in FIG. 1, the computer-executable application can be an electronic health record application (EHR); however, other implementations are also contemplated. For instance, the computer-executable application can be a web application that interfaces with an EHR, such that the EHR exposes at least some clinical data maintained by the EHR. For purposes of explanation only, in the exemplary system 100, the application is illustrated and described as being an EHR. Briefly, the application exposes a data model to genetics labs, such that genetic test results can be retained in a known, structured data format. The application also incorporates a cross-clinical ontology, which links clinical terminology to genetics terminology. As will be described in greater detail herein, the ontology can have a network-like structure, such that clinical terminology can be linked to multiple, individual genetic variants (and/or genes), and a single genetic variant can be linked to multiple clinical concepts. Further, the application can incorporate a knowledge base, which can include descriptions of genetic variants, links to external data sources (e.g., a wiki page), etc. In addition, the application uses a rules engine in order to calculate different cross clinical genomics rules and algorithms. Since the application retains data in accordance with the data model, and incorporates the ontology and knowledge base, the application can be configured to perform a variety of tasks: 1) provide information to a clinician that identifies specific genetic information related to a disease, symptom, etc.; 2) provide information to a clinician that identifies genetic test results, and further identifies diseases, symptoms, etc. that are related to the test results; 3) provide an indication (at the point of care) as to whether a patient would benefit from genetic testing; 4) provide a list of patients who would benefit from genetic testing; 5) provide a visualization that represents relationships between body systems, phenotypes, diseases, and genetics information; etc.

The system 100 includes a server computing device 102, a client computing device 104 that is in network communication with the server computing device 102, and a genetics lab computing device 106 that is in network communication with the server computing device 102. For instance, the server computing device 102 may be in network communication with the client computing device 104 by way of an intranet, and the server computing device 102 may be in communication with the genetics lab computing device 106 by way of the Internet.

The server computing device 102 includes a processor 108 and memory 110, wherein the memory 110 has the cross-clinical genetics application (e.g., the EHR) 112 loaded therein. has an electronic health record application (EHR) 112 loaded therein. The EHR 112 is well-suited for employment in a medical facility, and can be configured to perform a variety of computing tasks that assist the medical facility with providing care for patients. For instance, the EHR 112 can be configured with patient intake functionality, billing functionality, bed tracking functionality, tracking care provided to patients, and so forth. Contrary to conventional EHRs, the EHR 112 provides information to a clinician pertaining to genomic data, as will be described in greater detail below. The EHR 112 includes a rules engine 114, which is, for instance, configured to output an indication as to whether it would be beneficial for a patient or patients to undergo genetic testing based upon clinical data about the patient or patients. Further, the EHR 112 can be configured to receive genetic test results and output interpretations of the test results that are useful to a clinician, who is typically not a geneticist (and may otherwise find the genetic test results confusing).

The server computing device 102 includes a data repository 116, which includes data that is accessible to the EHR 112. While shown as being one data repository 116, it is to be understood that the data shown as being retained in the data repository 116 may be stored over multiple repositories. More specifically, the data repository 116 includes a cross-clinical ontology 118, which links clinical terminology and/or codes to genetic terminology and/or codes. At a high-level, then, the ontology 118 represents a disease (such as cancer) as a genomics representation, instead of as body-site related (e.g., lung cancer). Further, as mentioned above, the ontology 118 is cross-clinical, in that, in the ontology 118, a genetic variant can be a portion of a representation for several different diseases and/or disease types, and vice versa.

Figure 2:
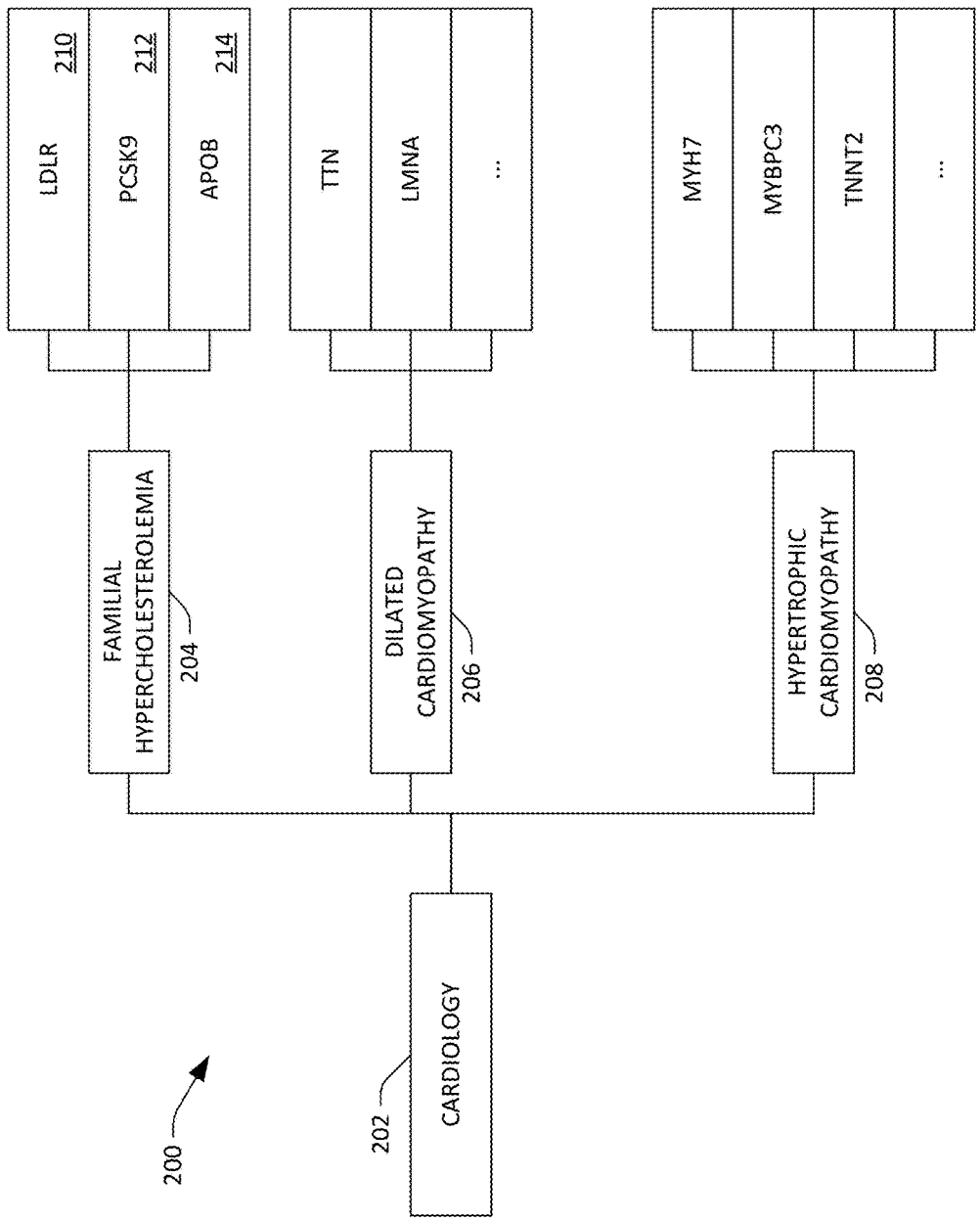

Referring briefly to FIGS. 2 and 3, a first exemplary portion 200 and a second exemplary portion 300, respectively, of the ontology 118 are presented, where the portions relate to cardiology. The portions 200 and 300 of the ontology 300 are represented as a tree-structure, with a root of the tree representing a branch of medicine (e.g., cardiology, oncology, etc.), and leaves of the tree representing low-level genetic information (e.g., alleles). As shown in FIG. 2, a root 202 of the tree represents cardiology, and the root 202 (in this example) has three children 204-208: 1) familial hypercholesterolemia; 2) dilated cardiomyopathy; and 3) hypertrophic cardiomyopathy. Each of these nodes has its own children. For instance, the node 204 has three children 210-214: 1) LDLR; 2) PCSK9; and 3) APOB. The nodes 210-214 can represent proteins and enzymes known to correspond to familial hypercholesterolemia. Turning solely to FIG. 3, the portion 300 of the ontology 118 includes the node 210, which can include information that pertains to LDLR with respect to familial hypercholesterolemia. The node 210 can include codes corresponding to different organizations used to identify the protein LDLR. The node 210 can also be coupled to several leaves (collectively associated with reference numeral 302), which can represent alleles that exhibit the protein LDLR as it corresponds to familial hypercholesterolemia. While not shown, the ontology 118 also can include nodes that are representative of clinical terms; for instance, the node 204 can include children that are representative of symptoms associated with familial hypercholesterolemia, co-occurring diseases, observable phenotypes, and the like. Thus, again, the ontology 118 relates clinical concepts with panomics concepts.

Returning to FIG. 1, the data repository 116 also includes clinical data 120. The clinical data 120 can optionally include (but is not limited to including) at least some of the following data: electronic health records, administrative data, claims data, disease registries, health surveys, and clinical trials data. The electronic health records can comprise administrative and demographic information, diagnoses, treatments, prescribed medications, (non-genetic) laboratory tests, hospitalization information, insurance information, and so forth. Administrative data can include hospital discharge information, which is often reported to a government agency. Claims data includes descriptions of billable interactions (insurance claims) between insured patients and the healthcare delivery system, wherein the claims data can be characterized as inpatient data, outpatient data, pharmacy data, and enrollment data. Disease registries include clinical information systems that track a range of data for certain chronic conditions such as Alzheimer's Disease, cancer, diabetes, heart disease, and asthma. Health surveys often include data collected for research purposes. Clinical trials data includes data collected over the course of clinical trials. As can be ascertained, the clinical data 120 can be pertinent to a single patient as well as pertinent to a population of patients.

The data repository 116 also includes genetics data 122, wherein the genetics data 122 can be received from computing systems of genetics labs (such as the genetics lab computing device 106). In another example, when the computer-executable application is an application that runs on top of an EHR, the genetics data 122 can be received from an EHR or multiple EHRs. For instance, for a patient, the genetics data 122 can identify genes tested, mutations identified, and so forth. The genetics data 122 can be formatted in accordance with a data structure exposed by the EHR 112. In other words, a genetics lab may be provided with the data structure, and can provide the server computing device 102 with genetics data in conformance with the data structure. In another example, the genetics lab can provide genetics data in some structured data format, and such data can be mapped into the above-referenced data structure. This in contrast to conventional approaches—conventionally, the genetics lab will submit a facsimile to a medical facility or submit an electronic document (e.g., a Portable Document Format document) to the medical facility, where data in the facsimile or electronic document is not readily parseable by the processor 108 of the server computing device 102. In the system 100, as the genetics data 122 is structured, the EHR 112 is able to search over the genetics data 122 and process the genetics data 120 to output search results.

The data repository 116 also includes a knowledge base 124, which comprises data that can be pointed to by the clinical data 120 and/or the genetics data 122. For instance, the knowledge base 124 can include descriptions about portions of the genetics data 122, as clinicians using the EHR 112 may be unfamiliar with genetics terminology. Additionally, the knowledge base 124 can include addresses to external data sources, which can be surfaced by the EHR 112 in hyperlinks when the EHR 112 provides the clinician with certain genetics-related information. Thus, if the clinician is unfamiliar with a code (for example), the EHR 112 can provide a hyperlink to a wiki page that describes a certain gene mutation based upon a URL in the knowledge base 124. Further, the knowledge base 124 can include interpretations of genetics information, which can be used by the clinician to optimize decisions about the care of a patient.

The client computing device 104 is operated by a clinician in a medical facility. The client computing device 104 includes a processor 126 and memory 128, wherein the memory 128 has a client application 130 loaded therein. The client computing device 104 may be any suitable type of computing device, including a kiosk, a desktop computing device, a laptop computing device, a tablet (slate) computing device, a personal digital assistant, a mobile telephone, a wearable computing device (e.g., a watch, wearable, etc.), a voice-assistant computing device, and so forth. The client application 130, when executed by the processor 126, is configured to communicate with the EHR 112. Therefore, the client application 130 can be a web browser that, when directed to a certain URL, is configured to communicate with the EHR 112. In another example, the client application 130 can be a client application dedicated to the EHR 112. In still yet another example, the client application 130 can be a personal assistant application (with functionality distributed between the client computing device 104 and another server computing device).

As indicated previously, the clinician operates the client computing device 104, and the client application 130 can be employed by the clinician to retrieve data about a patient or population of patients and/or enter data about a patient or population of patients. In a non-limiting example, the client computing device 104 can be operated by the clinician to cause the client application 130 to retrieve data about a certain patient to whom the clinician is going to be providing care. The data can include demographic information about the patient, medical history of the patient, and so forth. The client computing device 104 can further be operated by the clinician to cause the EHR 112 to request a genetics test for a patient or patients (based upon execution of a rule by the rules engine 114), where the request can be transmitted from the server computing device 102 to the genetics lab computing device 106.

While the system 100 has been described as having the architecture shown, other architectures are contemplated. For instance, another application may be in communication with the EHR, wherein the another application can comprise the rules engine 114 and can cause the genetics data 122 to be stored in the data repository 116 (or some other data repository) in accordance with the data structure referenced above. Such architecture may be well-suited for situations where the EHR 112 is a legacy application and is incapable of performing the acts described herein. In such an architecture, the clinical data 120 of the EHR 112 can be exposed to the another application, and the another application can leverage the ontology 118 to provide relevant genetics information to the clinician at the point of care. Further, the server computing device 102 can be a device in a cloud computing system, wherein functionality described herein as being performed by the server computing device 102 can be performed in a distributed manner by multiple computing devices.

Figure 4:
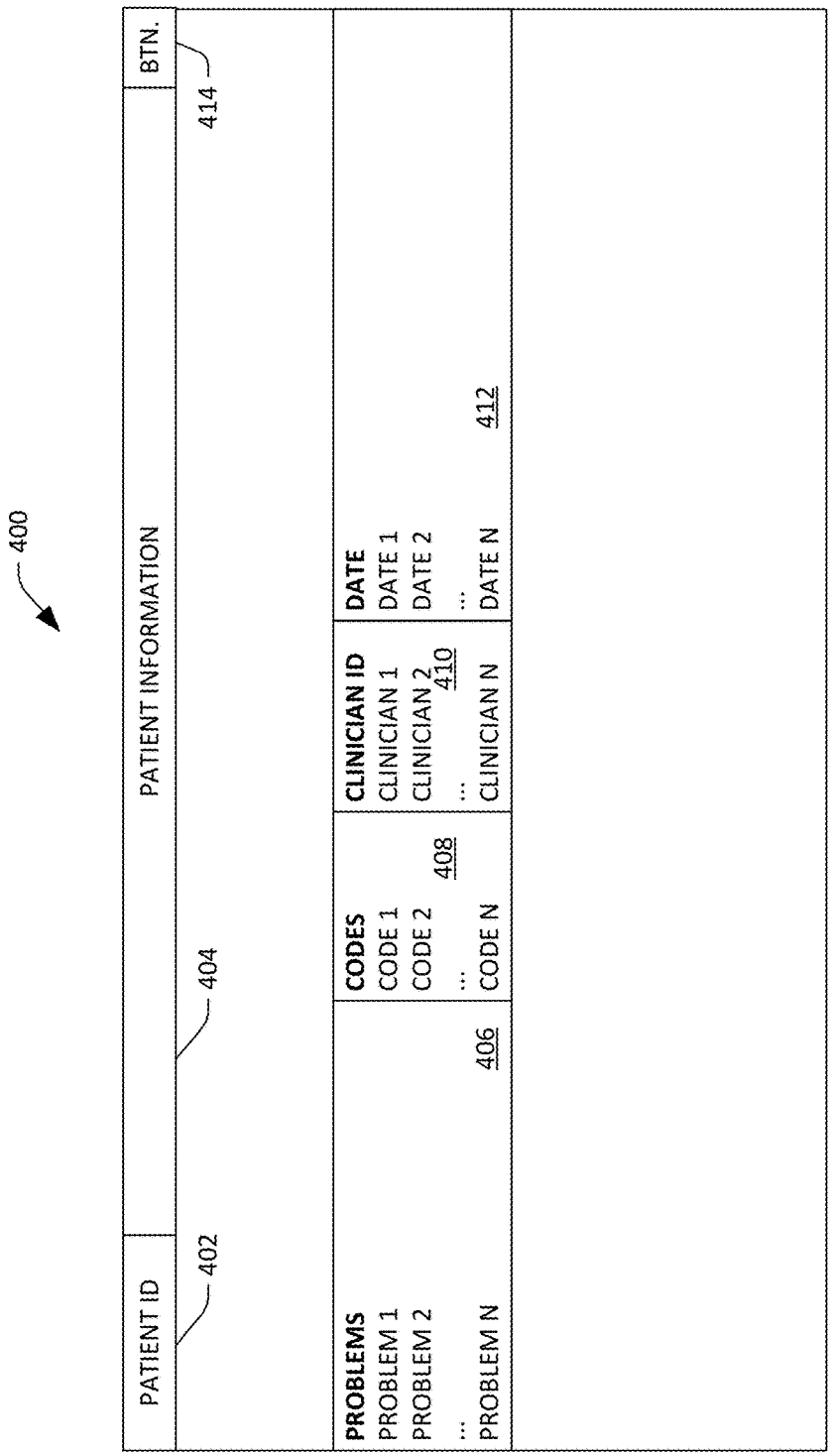

Operation of the system 100 will now be described with reference to FIGS. 4-11, which depict exemplary graphical user interfaces (GUIs) that may be presented on a display of the client computing device 104. Referring to FIG. 4, an exemplary GUI 400 that can be presented by the clinician who is operating the client computing device 104 is illustrated. The client computing device 104 is operated by the clinician to execute the client application 130, and to cause the client application 130 to provide data to the EHR 112. The data can include, for instance, an identity of a patient that is receiving care from the clinician. The EHR 112, in response to receiving the data, executes a search over the clinical data 120, the genetics data 122, and/or the knowledge base 124, and provides results of the search to the client application 130. The client application 130 causes the results of the search to be presented in the GUI 400 on the display of the client computing device 104.

The exemplary GUI 400 includes a patient identity 402, which can include a name of the patient and/or some other identifier of the patient. The GUI also includes patient information 404, such as date of birth, demographic information, contact information for the patient, and so forth. The GUI 400 further includes a field 406 that identifies health problems of the patient that are being tracked. These health problems can be chronic (e.g., obesity, hypertension) and/or acute (e.g., abdominal pain). The GUI 400 also includes a field 408 that identifies codes for the problems, such as ICD-9 and/or ICD-10 codes. A field 410 identifies clinicians monitoring the problem, and a field 412 identifies dates that indicate when treatment was most recently provided for the problem.

The GUI further comprises a button 414, which, when selected, can cause the client application 130 to present information pertaining to genetics about the patient on the display of the client computing device 104. For instance, the button 414 can include graphical data that indicates that genetics data about the patient (or a population that includes the patient) is available. Pursuant to an example, the graphical data on the button 414 can be an indication that the patient will benefit from a genetics test for one or more (or none) of the problems identified in the field 406. As noted previously, the rules engine 114 of the EHR 112 has access to the clinical data 120 of the patient in the data repository 116, as well as the ontology 118. The rules engine 114 (in this example), can execute a rule for a particular genetic disorder that receives at least some of the clinical data for the patient as input, where the rule is grounded in the knowledge Base 124. Execution of the rule can result in a determination that the patient may benefit from genetics testing for the genetic disorder, and the graphical data on the button 414 can indicate that the EHR 112 has made such determination. While the GUI 400 depicts the button 414, in other embodiments the GUI 400 can include a tab that pertains to genetic information. Further, the button 414 can be a "floating" button, which represents an entry point into the functionality described herein (e.g., where the application that is configured to perform the cross-clinical genomics functionality is an application that executes on top of an EHR). In other examples, the GUI 400 can have a popup that depicts cross-clinical genomics data, a separate page, etc.

Figure 5:
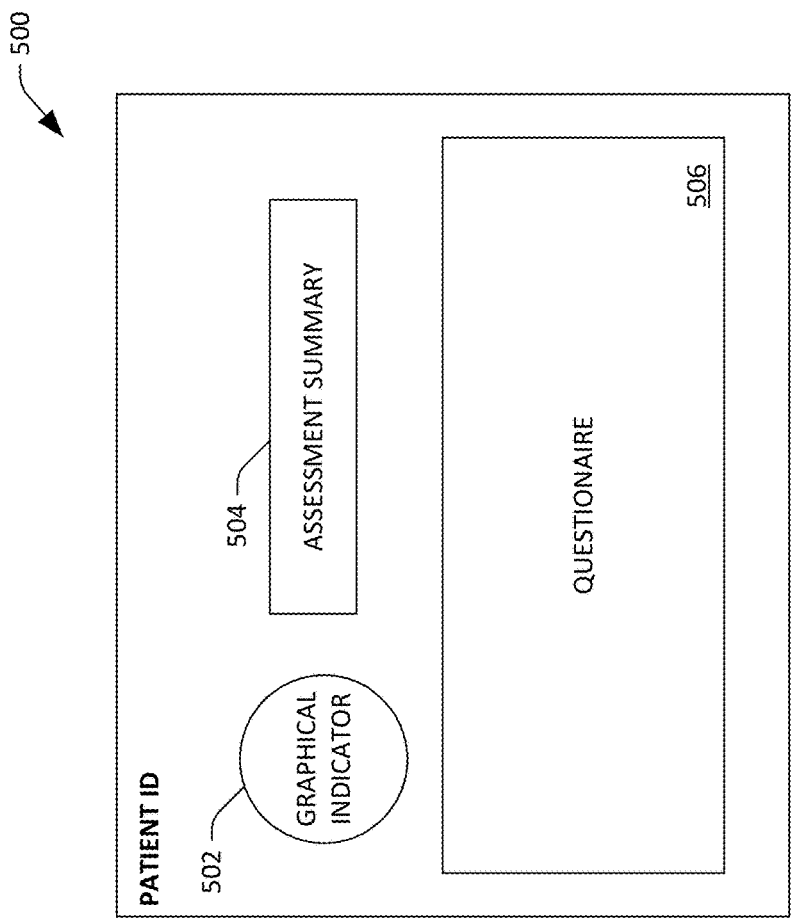

Now referring to FIG. 5, an exemplary GUI 500 that can be presented on the display of the client computing device 104 in response to a selection of the button 414 is illustrated. The GUI 500 includes the patient identifier, and optionally additional patient information. The GUI 500 also includes a graphical indicator 502 that indicates whether or not the patient is a candidate for genetic testing (for one or more diseases that may be associated with a genetic disorder). In an example, the graphical indicator 502 can include a score that is representative of a confidence that genetic testing will be beneficial when treating the patient. The GUI 500 can further include an assessment summary 504, which can be set forth to explain contents in the graphical indicator 502. For instance, the graphical indicator 502 can indicate that the patient is a strong candidate for genetic testing for premature coronary heart disease (CHD), and the assessment summary 504 can indicate that the candidate is a strong candidate for genetic testing based upon the patient having a relatively high LDL cholesterol level (in the clinical data 120).

The GUI 500 further includes a questionnaire 506 that can include one or more questions that, when answered, can refine the confidence that the genetic testing will be beneficial to the patient. For instance, the questions can be answered by "yes", "no", or "unsure" responses, each of which can be represented by buttons in the GUI 500. Exemplary questions that can be presented in the questionnaire include family history questions, such as whether any parent or sibling has had premature CHD, whether any parent, sibling, or child had LDL cholesterol above 190 mg/dl, and so forth. As the clinician sets forth answers to questions in the questionnaire 506, the graphical indicator 502 can be updated (e.g., the confidence that genetic testing will be beneficial to the patient changes based upon the answers to the questions). The questions in the questionnaire can be specified in the rule, where answers to the questions are not existent in the clinical data 120.

An exemplary rule is set forth below, where the rule is for familial hypercholesterolemia (FH), and is useable by the rules engine 114 to identify patients that would benefit from genetics testing when determining whether or not they can be diagnosed with FH.
Rule for FH
The patient will be identified as a candidate for genetic testing for FH if one of the following criteria exists:
 1) FH-relevant diagnosis or problem has been recorded for the patient
  a. Weight: 8
 2) Last LDL measurement is greater than or equal to 260 mg/dl
  a. Weight: 5.375 for 260, 8 for 330, and 10 for 400 and up
 3) Both criteria below exist:
  a. Last LDL >=240 mg/dl and <260 mg/dl
   i. Weight: 4.667 for 240, 5 for 250, and up to 5.375 for 260
  b. Ages 30-39
   i. Weight: 2 to ages=30 and up to 1 for the age of 39
 4) Both criteria below exist:
  a. Last LDL >=220 mg/dl and <260 mg/dl
   i. Weight: 4 for 220 and up to 5.375 for 260
  b. Ages 20-29
   i. Weight: 3 to ages=20 and up to 2 for the age of 29
 5) Both criteria below exist:
  a. Last LDL >=200 mg/dl and <260 mg/dl
   i. Weight 3.33 for 200 and up to 5.375 for 260
  b. Ages <20
   i. Weight: 4 to all ages <20
Patient will be excluded as a potential candidate if any of the following exist:
 1) Patient is not alive;
 2) Patient does not have a previous genetic test result;
 3) Patient has been diagnosed with diabetes
 4) Patient has a known mutation or genetic diagnosis in the family;
 5) The patient has a high level of triglycerides.
To obtain higher certainty, the following can be included in the questionnaire (which is not typically in the patient record):
 1) Patient has a premature CHD (<55 for men, <60 for women)? weight: 2
 2) Patient has tendon xanthoma? weight: 6
 3) Patient is on statins and has high LDL (after 3 months since medicine prescribed)? Weight: 2
 4) Patient has premature Corneal Arcus (<45)? weight: 4
 5) Patient has a premature cerebral or peripheral vascular disease (problem/diagnosis)? weight: 1
 6) Family has a history of FH? weight: 3
 7) Family has a history of Premature CHD (<55 for men, <60 for women)? weight 1
 8) Family has a history of tendon xanthoma? weight: 2
 9) Family has a history of Corneal Arcus? weight: 2

Figures 6, 7:
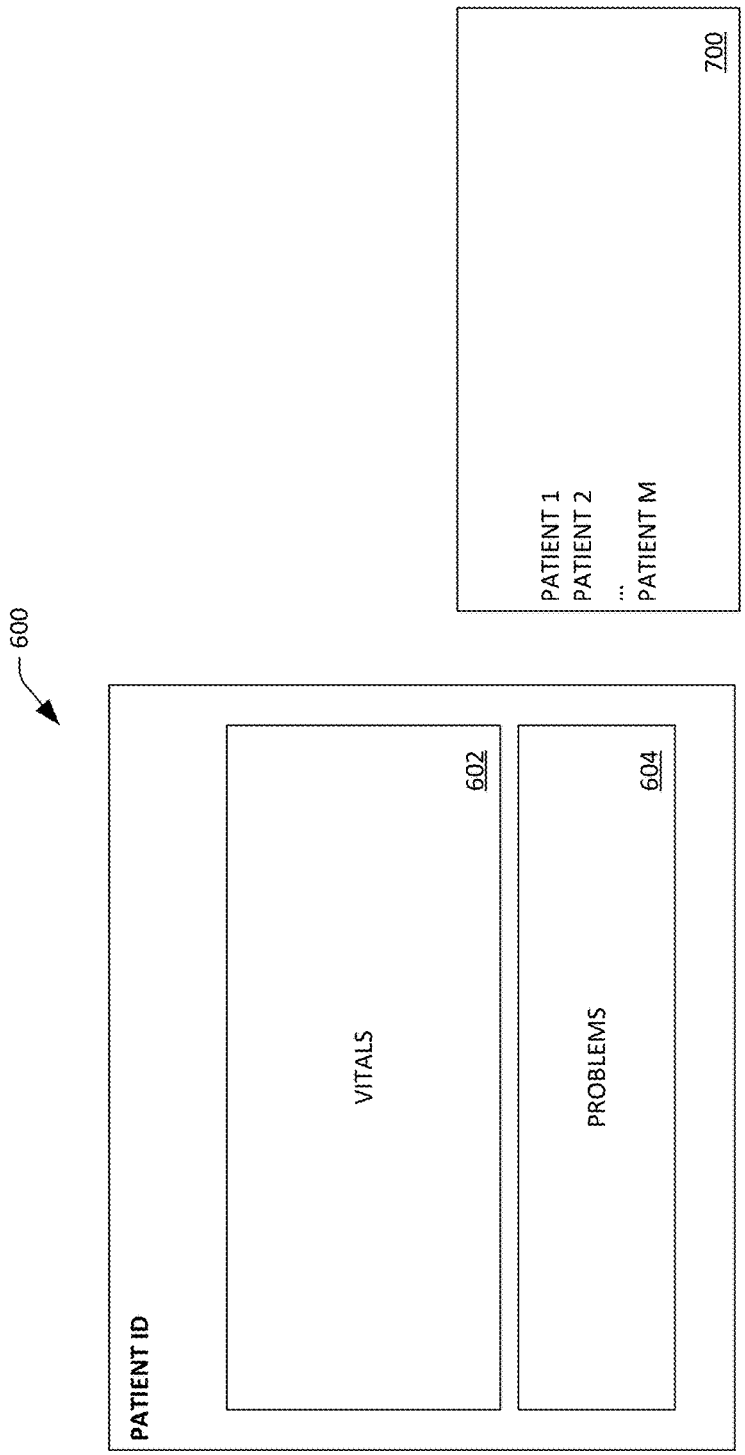

Now referring to FIG. 6, another exemplary GUI 600 that can be presented on the display of the client computing device 104 in response to the button 414 being selected is illustrated. The GUI 600 includes a field 602 that presents vitals of the patient, such as height, weight, BMI, body temperature, blood pressure, and the like. The vitals can be depicted graphically, as time-series data. The GUI 600 further includes a field 604 that identifies problems of the patient identified by the clinician. It is to be understood that an exemplary GUI can include features shown in the GUI 600 in combination with features shown in other GUIs, such that both genetics and relevant clinical data can be presented together.

With reference now to FIG. 7, an exemplary GUI 700 that depicts a list of patients that may benefit from genetic testing for the particular disorder (e.g., FH). For instance, the rules engine 114 of the 2 bp Core 112 can execute the rule referenced above over the clinical data 120 across several patients, and can identify patients that are likely to benefit from genetic testing for the disorder. As indicated above, the button 414 can include graphical data that indicates that a population has genetic information associated therewith. Selection the button 414 can, for example, cause the list of patients that may benefit from genetic testing to be presented in the GUI 700.

Figure 8:
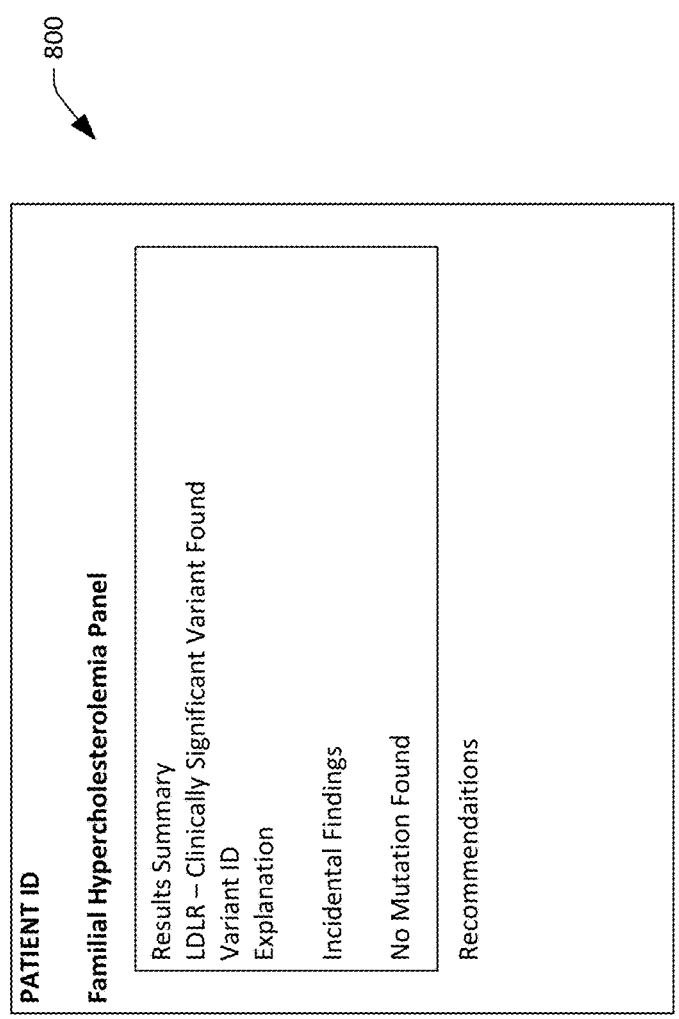

Now referring to FIG. 8, an exemplary GUI 800 that can be displayed on the display of the client computing device 104 is illustrated, where the GUI 800 depicts results of a genetics test for the patient, as well as information that is contemplatable by the clinician. For instance, the GUI 800 can identify that the genetic test was performed for FH, and can further indicate that a clinically significant variant for FH exists in the genome of the patient. The GUI 800 can identify the variant, and can further include an explanation as to why the variant is clinically significant. Such information can be retrieved from the knowledge base 124. The GUI 800 can also identify incidental findings to a tested gene. Still further, the GUI 800 can include recommendations for the clinician—such as to check for LDLR mutations in family members and/or order a genetic consultation. Further, the GUI 800 can depict relevant clinical information such as in GUI 600.

As indicated previously, the EHR 112 can cause such data to be presented in the GUI 800, since the genetics lab computing device 106 sets forth the genetics test results in a structured (schematized) format.

Now referring to FIG. 9, another exemplary GUI 900 is depicted, where the GUI 900 is well-suited for presenting lists of patients that may benefit for genetics testing for certain disorders. For instance, the GUI 900 can include a pulldown. The pulldown, when selected, presents a set of disorders for which the EHR 112 has rules (similar to the FH rule presented above). The clinician can select a disorder from the pulldown, and the EHR 112 can return the list of patients that are candidates for genetic testing for the selected disorder to the client computing device 104. The EHR 112 can execute the rule for the selected disorder over the clinical data 120 in real-time, or can generate the lists of patients in the background. The GUI 900 includes additional filter options, such that patients in the list can be filtered by gender, age, score, test value, primary care physician, etc.

Figure 10:
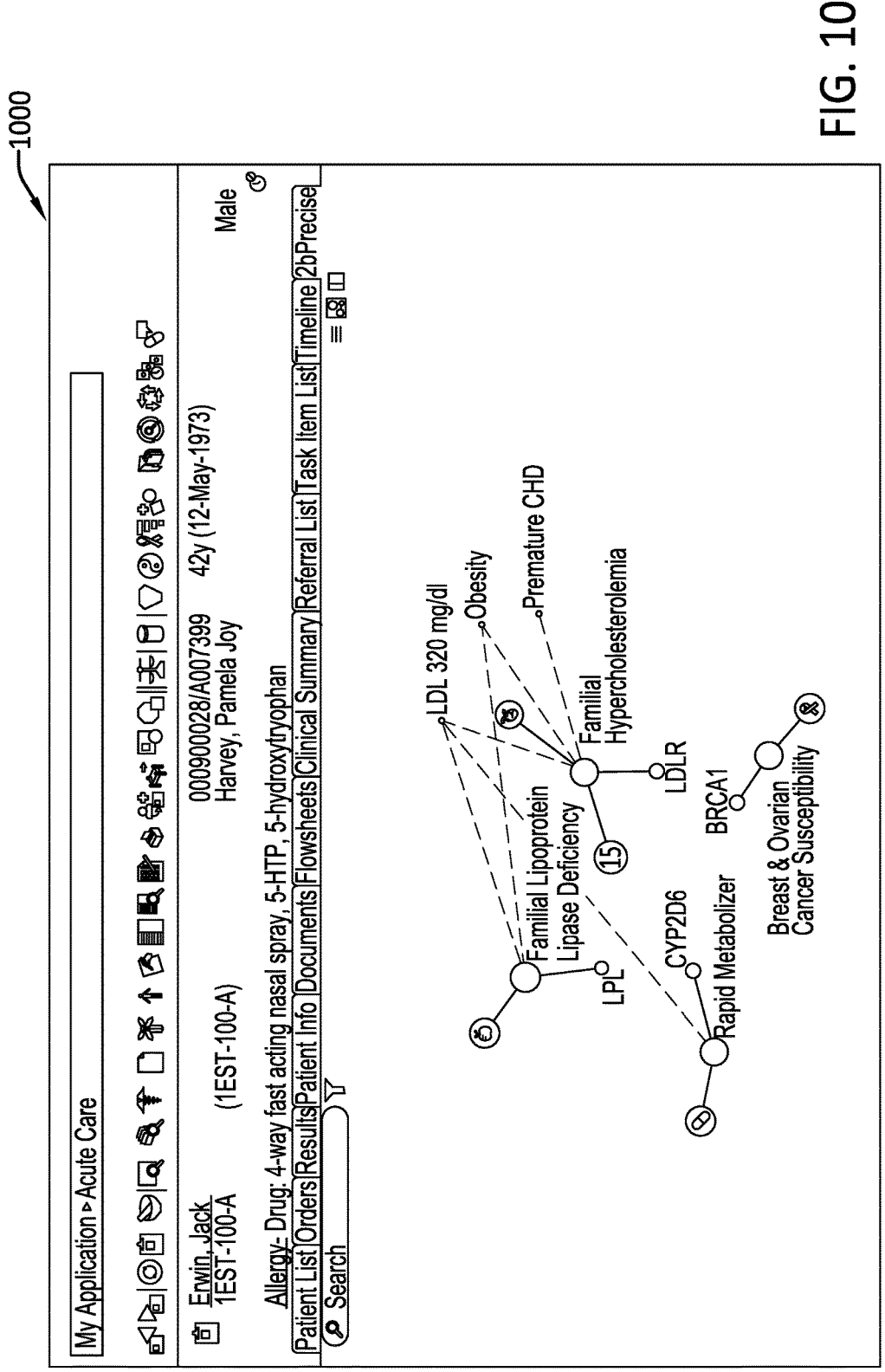

Turning to FIG. 10, an exemplary GUI 1000 that can be presented on the display of the client computing device 104 based upon genetic test results received from the genetics computing device 106. The GUI 1000 includes a visualization, where the visualization comprises a ring of icons, each icon being representative a body system. In the visualization, icons are highlighted when genetic results are related to the body systems. The visualization also includes an inner ring of icons, which represent genetic disorders for the body system. The visualization further includes still further icons that are representative of genetic mutations found in the test results, where the mutations are germane to the disorder. For example, a first icon can represent a body system of the heart, a second icon (connected to the first icon) can represent a genetic disorder of the heart (FH), a third icon (connected to the second icon) can represent a mutation of LDLR. Other icons related to FH can also be displayed as being connected to the second icon. Still further, phenotypes exhibited by the patient and associated with FH can be represented in the visualization (e.g., obesity, high LDL, premature CHD).

Figure 11:
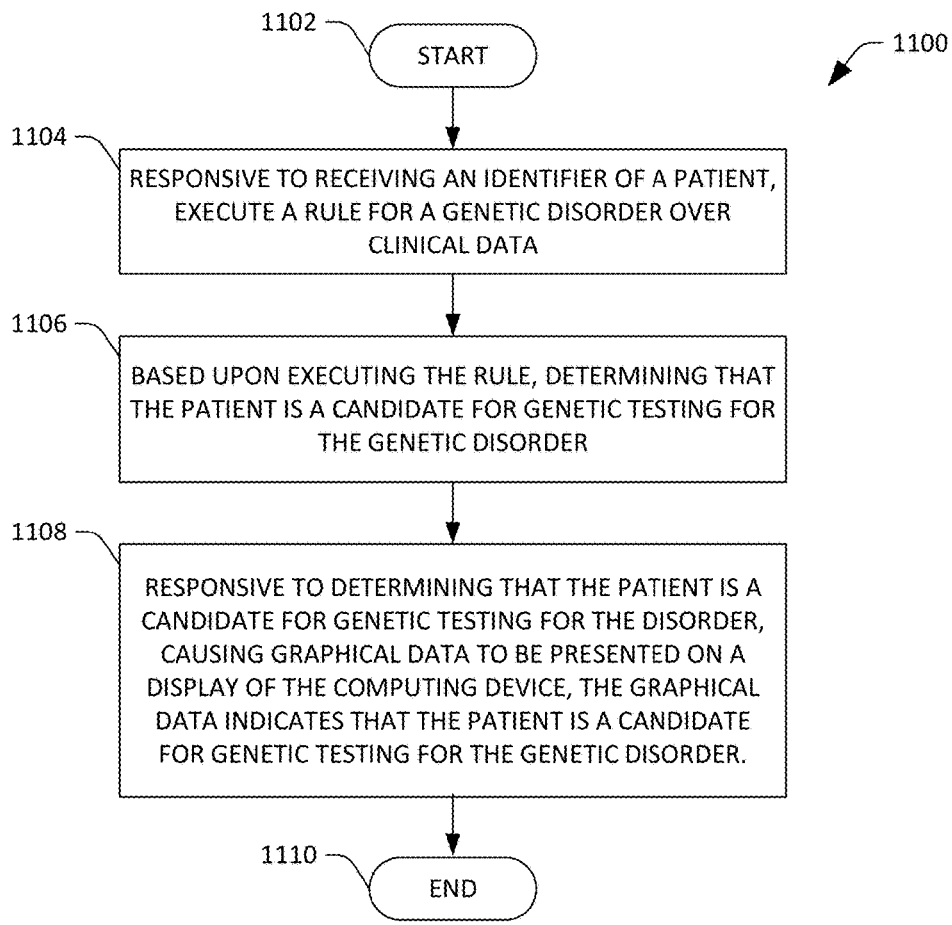
FIG. 11 is a flow diagram that illustrates an exemplary methodology for graphically indicating that a patient will benefit from acquiring a genetic test for a genetic disorder.
Figure 12:
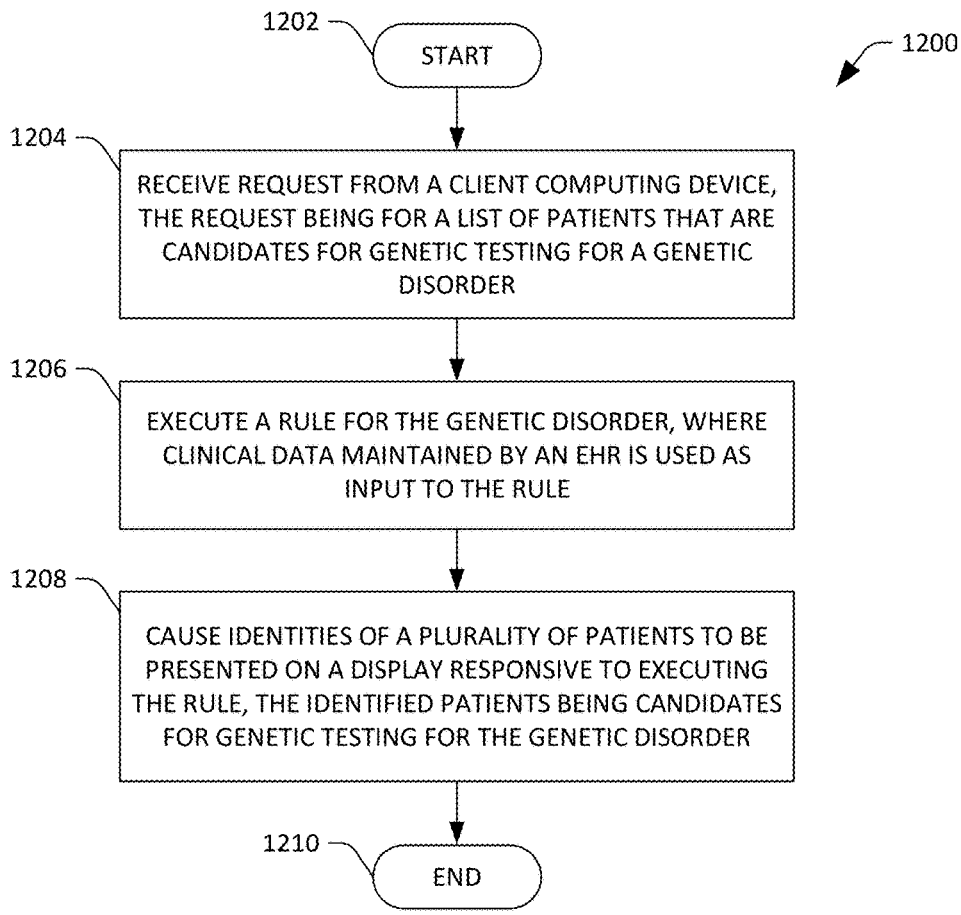
FIG. 12 is a flow diagram that illustrates an exemplary methodology for identifying a list of patients that will benefit from genetic testing for a specified genetic disorder.

FIGS. 11 and 12 illustrate exemplary methodologies relating to utilizing clinical data maintained by an EHR to ascertain whether a patient will benefit from genetic testing. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Turning solely now to FIG. 11, an exemplary methodology 1100 for outputting an indication that a patient will benefit from genetic testing is illustrated. In an example, the methodology 1100 can be performed by at least one processor that executes an application. For instance, the application can be an EHR. In another example, the application can be a web application that interfaces with an EHR, such that the web application is able to access at least some clinical data maintained by the EHR. The methodology 1100 starts at 1102, and at 1104, responsive to receiving an identifier of a patient, a rule for a genetic disorder is executed over clinical data that is accessible to the application, wherein the clinical data is about the patient. For instance, the clinical data can include an electronic health record of the patient.

At 1106, based upon executing the rule, determining that the patient is a candidate for genetic testing for the genetic disorder. At 1108, responsive to determining that the patient is a candidate for genetic testing for the genetic disorder, causing graphical data to be presented on a display of the computing device, the graphical data indicating to a clinician that the patient is a candidate for genetic testing for the disorder. For instance, the graphical data can indicate a confidence that the genetic testing will be beneficial to the patient. Subsequently, the computing device can be operated by a clinician to cause the genetic testing to be ordered from a genetics lab. The methodology 1100 completes at 1110.

Now referring to FIG. 12, an exemplary methodology 1200 for identifying a plurality of patients that are candidates for genetic testing for a genetic disorder is illustrated. The methodology 1200 starts at 1202, and at 1204 a request is received from a client computing device, where the client computing device is operated by a clinician. The request specifies a genetic disorder. At 1206, responsive to receiving the request, a rule for the genetic disorder is executed, wherein data from electronic health records maintained by an EHR is used as input to the rule. In an example, the rule can output a score for a plurality of patients who have electronic health records maintained by the EHR, and the patients can be ordered based upon the scores. At 1208, identities of a plurality of patients can be presented on a display of the computing device, where each patient in the plurality of patients has a score assigned thereto that is above a threshold. The methodology 1200 completes at 1210.

Figure 13:
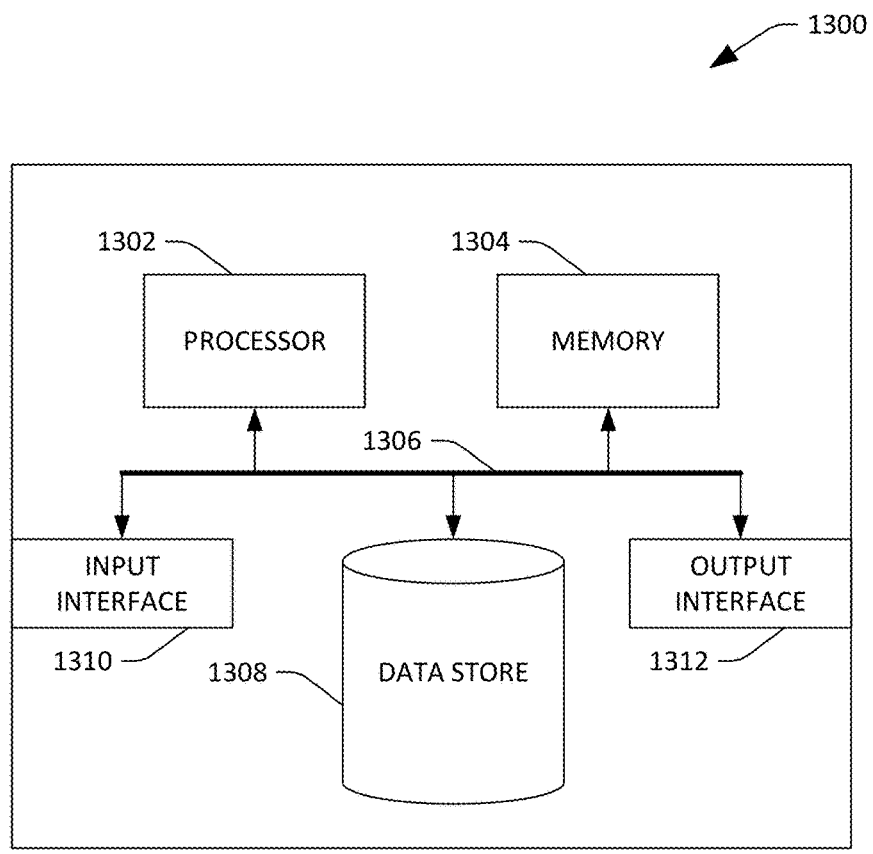
FIG. 13 is an exemplary computing system.

Referring now to FIG. 13, a high-level illustration of an exemplary computing device 1300 that can be used in accordance with the systems and methodologies disclosed herein is illustrated. For instance, the computing device 1300 may be used in a system that executes an EHR. By way of another example, the computing device 1300 can be used in a system that executes a supplement application. The computing device 1300 includes at least one processor 1302 that executes instructions that are stored in a memory 1304. The instructions may be, for instance, instructions for implementing functionality described as being carried out by one or more components discussed above or instructions for implementing one or more of the methods described above.

The processor 1302 may access the memory 1304 by way of a system bus 1306. In addition to storing executable instructions, the memory 1304 may also store patient-centric data, population data, etc.

The computing device 1300 additionally includes a data store 1308 that is accessible by the processor 1302 by way of the system bus 1306. The data store 1308 may include executable instructions, patient-centric data, population data, etc. The computing device 1300 also includes an input interface 1310 that allows external devices to communicate with the computing device 1300. For instance, the input interface 1310 may be used to receive instructions from an external computer device, from a user, etc. The computing device 1300 also includes an output interface 1312 that interfaces the computing device 1300 with one or more external devices. For example, the computing device 1300 may display text, images, etc. by way of the output interface 1312.

It is contemplated that the external devices that communicate with the computing device 1300 via the input interface 1310 and the output interface 1312 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 1300 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 1300 may be a distributed system. Thus, for instance, several devices may be in communication by way of a network connection and may collectively perform tasks described as being performed by the computing device 1300.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A computing system comprising:
at least one processor; and
memory that has an application loaded therein, wherein the application, when executed by the at least one processor, is configured to perform acts comprising:
responsive to receipt of an identifier of a patient:
retrieving clinical data about the patient based upon the identifier of the patient, the clinical data being accessible by the application and identifies health problem of the patient;
applying a rule for a genetic disorder to the health problem identified in the clinical data;
determining using the rule that the patient is a candidate for genetic testing for the genetic disorder;
causing graphical data to be presented on a display of a computing device, the graphical data indicating to a clinician that the patient is a candidate for genetic testing for the genetic disorder;
based upon determining that the patient is a candidate for genetic testing for the genetic disorder, transmitting an order for a genetic test for the genetic disorder to a genetics lab computing device that is in network communication with the computing system;
receiving results for the genetic test from the genetics lab computing device; and
causing a visualization based upon the results to be presented on the display of the computing device, wherein the visualization is based on a relationship between:
a body system affected by the genetic disorder;
the genetic disorder; and
a genetic mutation associated with the genetic disorder, and further wherein the visualization comprises:

a first group of icons assigned to body systems of the patient, the body system that is affected by the genetic disorder is included in the body systems;

a second group of icons assigned to genetic disorders of the body systems, the genetic disorder is included in the genetic disorders; and a third group of icons assigned to genetic mutations that cause the genetic disorders, the genetic mutation that is associated with the genetic disorder that is tested for in the genetic test is included in the genetic mutations, wherein the relationship is indicated in the visualization by a visually perceptible connection between a first icon corresponding to the body system from the first group, a second icon corresponding to the genetic disorder from the second group, and a third icon corresponding to the genetic mutation from the third group, the relationship being between the body system, the genetic disorder, and the genetic mutation.

2. The computing system of claim 1, the acts further comprising:
subsequent to causing the graphical data to be presented on the display of the computing device, receiving an indication from the computing device that a genetic test is to be ordered for the patient, wherein transmitting the order occurs responsive to receiving the indication.

3. The computing system of claim 2, wherein the results for the genetic test are in a structured format the acts further comprising:
storing the results for the genetic test in a data repository in accordance with a predefined data model.

4. The computing system of claim 3, the acts further comprising:
subsequent to storing the results for the genetic test in the data repository in accordance with the predefined data model, receiving a request from the computing device to review the results for the genetic test, wherein causing the visualization to be presented on the display of the computing device occurs.

5. The computing system of claim 1, the application being an electronic health record application (EHR), and the clinical data comprises an electronic health record for the patient maintained by the EHR.

6. The computing system of claim 1, the application being a web application that is in communication with an EHR, wherein the web application receives the clinical data from the EHR.

7. The computing system of claim 1, wherein the first group of icons, the second group of icons, and the third group of icons are arranged in a first ring, a second ring, and a third ring, respectively, wherein the third ring is located within the second ring, wherein the second ring is located within the first ring.

8. A method executed by at least one computer processor of a computing system, the method comprising:
responsive to receipt of an identifier of a patient:
retrieving clinical data about the patient based upon the identifier of that identifies a health problem of the patient:
applying a rule for a genetic disorder to the health problem identified in the clinical data;
determining using the rule that the patient is a candidate for genetic testing for the genetic disorder;
causing graphical data to be presented on a display of a computing device, the graphical data indicating to a clinician that the patient is a candidate for genetic testing for the genetic disorder;
based upon determining that the patient is a candidate for genetic testing for the genetic disorder, transmitting an order for a genetic test for the genetic disorder to a genetics lab computing device that is in network communication with the computing system:
receiving results for the genetic test from the genetics lab computing device; and
causing a visualization based upon the results to be presented on the display of the computing device, wherein the visualization is based upon a relationship between:
a body system affected by the genetic disorder;
the genetic disorder; and
a genetic mutation associated with the genetic disorder, and further wherein the visualization comprises:
a first group of icons assigned to body systems of the patient, the body system that is affected by the genetic disorder is included in the body systems;
a second group of icons assigned to genetic disorders of the body systems the genetic disorder is included in the genetic disorders: and
a third group of icons assigned to genetic mutations that cause the genetic disorders, the genetic mutation tested for in the genetic test that is associated with the genetic disorder is included in the genetic mutations, wherein the relationship is indicated in the visualization by a visually perceptible connection between a first icon corresponding to the body system from the first group, a second icon corresponding to the genetic disorder from the second group, and a third icon corresponding to the genetic mutation from the third group, the relationship being between the body system, the genetic disorder, and the genetic mutation.

9. The method of claim 8, further comprising:
subsequent to causing the graphical data to be presented on the display of the computing device, receiving an indication from the computing device that a genetic test is to be ordered for the patient, wherein transmitting the order occurs responsive to receiving the indication.

10. The method of claim 9, wherein the results for the genetic test are in a structured format, the method further comprising:
storing the results for the genetic test in a data repository in accordance with a predefined data model.

11. The method of claim 10, further comprising:
subsequent to storing the results for the genetic test in the data repository in accordance with the predefined data model, receiving a request from the computing device to review the results for the genetic test wherein causing the visualization to be presented on the display of the computing device occurs responsive to receiving the request.

12. The method of claim 8, the application being an electronic health record application (EHR), and the clinical data comprises an electronic health record for the patient maintained by the EHR.

13. The method of claim 8, the application being a web application that is in communication with an electronic health record application (EHR), wherein the web application receives the clinical data from the EHR.

14. The method of claim 8, wherein the first group of icons, the second group of icons, and the third group of icons are arranged in a first ring, a second ring, and a third ring, respectively, wherein the third ring is located within the second ring, wherein the second ring is located within the first ring.

15. A non-transitory computer-readable storage medium comprising instructions that, when executed by at least one processor of a computing system, cause the at least one processor to perform acts comprising:
responsive to receipt of an identifier of a patient:
retrieving clinical data about the patient based upon the identifier of the patient that identifies a health problem of the patient;
applying a rule for a genetic disorder to the clinical data;
determining, using the rule, that the patient is a candidate for genetic testing for the genetic disorder;
causing graphical data to be presented on a display of a computing device, the graphical data indicating to a clinician that the patient is a candidate for genetic testing for the genetic disorder;
based upon determining that the patient is a candidate for genetic testing for the genetic disorder, transmitting an order for a genetic test for the genetic disorder to a genetics lab computing device that is in network communication with the computing system;
receiving results for the genetic test from the genetics lab computing device; and
causing a visualization based upon the results to be presented on the display of the computing device, wherein the visualization is based upon a relationship between:
a body system affected by the genetic disorder;
the genetic disorder; and
a genetic mutation associated with the genetic disorder, and further wherein the visualization comprises:
a first group of icons assigned to body systems of the patient, the body system that is affected by the genetic disorder is included in the body systems;
a second group of icons assigned to genetic disorders of the body systems the genetic disorder is included in the genetic disorders: and
a third group of icons assigned to genetic mutations that cause the genetic disorders, the genetic mutation tested for in the genetic test that is associated with the genetic disorder is included in the genetic mutations,
wherein the relationship is indicated in the visualization by a visually perceptible connection between a first icon corresponding to the body system from the first group, a second icon corresponding to the genetic disorder from the second group, and a third icon corresponding to the genetic mutation from the third group, the relationship being between the body system, the genetic disorder, and the genetic mutation.

16. The non-transitory computer-readable storage medium of claim 15, the acts further comprising:
subsequent to causing the graphical data to be presented on the display of the computing device, receiving an indication from the computing device that a genetic test is to be ordered for the patient wherein transmitting the order occurs responsive to receiving the indication.

17. The non-transitory computer-readable storage medium of claim 16, wherein the results for the genetic test are in a structured format, the acts further comprising:
storing the results for the genetic test in a data repository in accordance with a predefined data model.

18. The non-transitory computer-readable storage medium of claim 17, the acts further comprising:
subsequent to storing the results for the genetic test in the data repository in accordance with the predefined data model, receiving a request from the computing device to review the results for the genetic test wherein causing the visualization to be presented on the display of the computing device occurs responsive to receiving the request.

19. The non-transitory computer-readable storage medium of claim 15, wherein the first group of icons, the second group of icons, and the third group of icons are arranged in a first ring, a second ring, and a third ring, respectively, wherein the third ring is located within the second ring, wherein the second ring is located within the first ring.

20. The non-transitory computer-readable storage medium of claim 15, the application being an electronic health record application (EHR), and the clinical data comprises an electronic health record for the patient maintained by the EHR.

* * * * *